(12) United States Patent
Weaver et al.

(10) Patent No.: US 6,472,151 B1
(45) Date of Patent: Oct. 29, 2002

(54) METHOD OF SCREENING FOR COMPOUNDS THAT MODULATE THE ACTIVITY OF A MOLECULAR TARGET

(75) Inventors: C. David Weaver, Wallingford; Todd A. Verdoorn, Higganum, both of CT (US); Gordon W. Robinson, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/370,847

(22) Filed: Aug. 10, 1999

Related U.S. Application Data

(60) Provisional application No. 60/097,065, filed on Aug. 19, 1998.

(51) Int. Cl.[7] .......................... C12Q 1/68; C12N 15/09; C12N 15/00; C12P 21/06; C07H 21/04
(52) U.S. Cl. .......................... 435/6; 435/69.1; 435/325; 435/320.1; 435/440; 435/455; 435/471; 435/476; 435/4; 435/29; 536/23.1
(58) Field of Search .......................... 435/4, 6, 29, 243, 435/325, 410, 440, 455, 471, 476; 536/23.1

(56) References Cited

U.S. PATENT DOCUMENTS

| 4,816,395 A | | 3/1989 | Hancock et al. |
| 5,552,290 A | | 9/1996 | Michelson et al. |
| 5,645,988 A | | 7/1997 | Vande Woude et al. |
| 5,955,275 A | | 9/1999 | Kamb |
| 5,977,305 A | * | 11/1999 | Wigler et al. ................ 530/350 |
| 6,001,963 A | * | 12/1999 | Bergsma et al. ............ 503/324 |
| 6,159,705 A | * | 12/2000 | Trueheart et al. ............. 435/29 |

FOREIGN PATENT DOCUMENTS

WO    WO97/27212    7/1997

OTHER PUBLICATIONS

Anderson et al, Proceedings of the National Academy of Sciences, USA 89: 3736–3740, May 1992.*

* cited by examiner

*Primary Examiner*—David Guzo
*Assistant Examiner*—Gerald G. Leffers, Jr.
(74) *Attorney, Agent, or Firm*—Audrey F. Sher; Christopher A. Klein

(57) ABSTRACT

The present invention provides a method for generating and isolating cell lines that functionally express molecular targets for drug discovery without utilizing information from the nucleic acid or amino acid sequence of the target protein. This procedure for the first time allows one to develop fast, high throughput screens for evaluation of test compounds that may modulate molecular targets whose specific nucleic acid or amino acid sequences are unavailable.

14 Claims, No Drawings

METHOD OF SCREENING FOR COMPOUNDS THAT MODULATE THE ACTIVITY OF A MOLECULAR TARGET

This application is a nonprovisional application that claims priority to provisional application Ser. No. 60/097,065 filed Aug. 19, 1998.

FIELD OF THE INVENTION

The present invention provides a method for functionally expressing and isolating molecular targets for drug discovery without utilizing information about the nucleic acid or amino acid sequence of the target under study. This procedure for the first time allows one to develop fast high throughput screens against molecular targets whose specific nucleic acid and amino acid sequences are not available. Screening tools such as cell lines or Xenopus oocytes are generated by expression of cDNA libraries and validated based on the pharmacological and physiological properties of the desired protein. No specific sequence information (e.g., purified or isolated nucleic acid sequences) is necessary to practice the screening tool of the present invention.

BACKGROUND OF THE INVENTION

Obtaining isolated cDNA clones of potential molecular targets for drug discovery is a standard method used throughout the pharmaceutical industry. Such clones often allow more facile screening against libraries of potential therapeutic compounds. For example, if one wishes to screen for compounds that modulate the activity of inosine 5'-monophosphate dehydrogenase ("IMPDH"), the nucleic acid sequence is useful to manufacture recombinant protein and run a screen. (See, e.g., U.S. Pat. No. 5,665,583).

At present, molecular targets are cloned using available nucleic acid or protein sequence information, and polymerase chain reaction ("PCR") or homology screening. Verification is accomplished by characterizing the functional or physical properties of the potential target. It is important to note that the functional properties of the protein are of greatest value to drug discovery. In many cases the nucleic acid or amino acid sequences are of lessor interest and value.

One common approach to identifying the nucleic acid sequence of a molecular target is referred to as expression cloning. A single cDNA is isolated and cloned based on its ability to direct the synthesis of a functional protein. The properties conferred upon host cells are used as the endpoint in the search for an appropriate cDNA clone. Normally, this individual cDNA is then sequenced. However, availability or knowledge of the sequence (or lack thereof) does not alter the ability to functionally characterize the expressed protein or to use it in a screen. A major drawback to this historic method of screening molecular targets is that expression cloning is laborious and time consuming. Newer technology for detecting the actions of receptors, enzymes and ion channels has made this task markedly easier.

The present invention for the first time presents a new method for combining classical expression cloning with high sensitivity methods for detecting functional proteins in host cells to produce molecular and cellular tools for high throughput screens and other drug discovery efforts. The novelty of this method is that desired endpoint of DNA manipulation is not the isolation and sequencing of a single DNA molecule, but rather the generation of cells and cell lines that express a particular desired phenotype. This approach provides significant advantages over current screening methods that rely upon expression cloning and sequencing, and facilitates the efforts of those skilled in the art to find molecules that interact with nearly any human protein and develop drugs that target these proteins.

SUMMARY OF THE INVENTION

The present invention provides a novel method for generation of cells and cell lines and to screen for compounds that interact with, and potentially modulate the activity of, a given molecular target. The present invention eliminates the need to isolate and clone a specific nucleic acid sequence encoding the molecular target. Rather, the method relies upon techniques such as retroviral activation of cellular gene transcription and detecting the functional or physical properties of the potential target. The present method is quicker than the screening methods of the prior art, and is adaptable to test compounds against any molecular target protein.

DETAILED DESCRIPTION OF THE INVENTION

Functional or expression cloning provides a method of expressing, isolating, and maintaining clones of potential targets of therapeutic intervention. Messenger RNA ("mRNA") is isolated by methods known in the art. Preferably, the MRNA is isolated from tissue known to express a certain molecular target of interest. In one embodiment, using known methods (Chirgwin et al., (1979) *Biochem.* 18:5294–5299), the isolated mRNA is reverse transcribed to produce a "library" of cDNAs, which ideally will contain full length copies of all mRNAs expressed in that tissue. The library of cDNAs is then subcloned into commercially available vectors that are optimized to express proteins encoded by the cDNAs in a host cell, for example in mammalian cells, Xenopus oocytes, *E. coli,* or yeast.

The library is then subdivided into pools containing any number of individual clones, for example 1000–5000 individual clones, per pool. Expression is accomplished by introducing individual pools of the library into the appropriate host cells and testing for functional activity with a variety of assays. The exact host cell and measured endpoint will depend on the nature of the molecular target one wishes to test.

Once a pool containing the cDNA of the molecular target is identified, that cDNA pool is preferably further subdivided until a single cDNA that confers the appropriate function is found. Reduction to a single plasmid DNA is not necessary because permanent cell lines could be made from a mixture of cDNAs based solely on the fact that the final clonal line responded in a fashion expected of the molecular target.

If further molecular biological manipulations are necessary, such as for example high level expression in baculovirus-infected Sf9 cells, a plasmid comprising the recombinant DNA will be "rescued" from the transfected cells. Chromosomal DNA may then be isolated from positive cells and amplified by PCR with primers that recognize the flanking sequences from the original expression vector. The resulting PCR fragment is subcloned into a baculovirus shuttle vector for development of the appropriate recombinant virus.

Once a pool, or single cDNA, that confers an appropriate function is found, test chemical compounds can be screened to determine if they have an affect on the function of the specific molecular target. The term "chemical compound" encompasses proteins, peptides, and other molecules. This method never requires the use of an isolated nucleic acid sequence that encodes the actual target molecule.

In another embodiment, this invention utilizes the propensity of certain RNA-based viruses, known as retroviruses or tumor viruses, to efficiently infect and then integrate DNA copies of their genome (or proviruses) into the chromosomal DNA of a host cell. The mechanism of integration varies among retroviruses, but is fairly non-specific in terms of chromosomal integration sites. Significantly, proviral integration often results in the physical linkage of strong viral expression elements (long terminal repeat enhancers) proximal to inactive or weakly active cellular genes. At some frequency, this results in the aberrant over-expression of the cellular gene, a phenomenon known as transcriptional activation. Retroviral activation of oncogenes has been very well documented. If the over-expressed RNA is translated to produce a target protein that has sufficient activity in the host cell, such a cell can be detected in a screening assay based on a functional or physical property of the protein. It follows that in a sufficiently large pool of retrovirally infected cells, a panel of cellular genes potentially including every one in the genome will be activated by different integration events, and from this population, a cell over-producing any particular molecular target can be identified, isolated and propagated indefinitely. The method of this invention thus comprises the following sequential steps: 1) infection of host cells with an integrating retrovirus to generate a large pool of chromosomally modified cells; 2) identification of cell(s) in the pool with a phenotype characteristic of a particular molecular target; 3) isolation and propagation of those cells as a stable line; and 4) screening of compounds for those that modulate the target protein's function in assays based on use of this stable cell line.

Certain methods of practicing this invention are preferred over others. In particular, use of engineered retroviruses that can infect human cells and immortalized cell lines (e.g. HeLa cells) are preferred, since they will be most useful in the over-production of human versus animal target proteins. Also preferred are genetically crippled retroviruses that fail to propagate or make infectious virus once they integrate, since these will yield safe, stable cell lines for screening test compounds. Additionally, the preferred retrovirus will contain a selectable marker (e.g., for G418 or puromycin resistance) driven by a viral enhancer element such that cells bearing an integrated provirus can be selected and will stably maintain activation of the target gene. The preferred retrovirus will also contain a viral enhancer element (e.g., cytomegalovirus promoter element) whose transcriptional activity is functional in most mammalian cells or one that can be specifically stimulated by an exogenous compound (e.g., glucocorticoids, tetracycline). Preferred as host cells are immortalized cell lines of mammalian origin (e.g., HeLa, HEK, HepG2, BHK) whose growth properties make them suitable for indefinite culture in vitro. All the retroviruses and cell lines described above are familiar to those experienced in the art.

Using the methods of the present invention one can identify a ligand that is capable of binding to and modulating the activity of a molecular target, such as a cell surface receptor. The word "modulating" refers to enhancement, diminishment, activation, inactivation and/or allosteric alteration of activity. The method comprises contacting a pool of cells or individual cell line(s) that exhibit(s) a desired functional activity with a potential ligand and measuring activity of the cell(s). The test ligand may be, for example, a protein, peptide, or other molecule.

The invention also provides a method of screening test compounds to identify compounds which interact with a specific cellular functional activity. This method comprises contacting a cell or cells that exhibit a specific activity with a plurality of test compounds, and detecting which drugs interact with and/or modulate the activity of the cell or cells. In some instances it may be desirable to identify chemical compounds that inhibit the activity of the specific molecular target, while in other instances it may be desirable to identify chemical compounds that activate or enhance the activity of the molecular target; both instances fall within the scope of the present invention. Various methods of detection may be used in the present invention.

Additionally, the test compounds may be labeled by association with a detectable marker substance (e.g., radiolabel or a non-isotopic label such as biotin). Test compounds may be selected by choosing compounds that bind, for example, to a cell surface receptor, using radioligand binding methods well known in the art.

Molecular targets of interest may be any molecule or protein in or on a cell that is involved in cell functioning. For example, potential targets include cell surface receptors, transcription proteins, ion channels, G-protein coupled receptors, protein kinases, protein phosphasates, or proteases.

The following examples are meant to be illustrative of embodiments of the present invention and do not limit the scope of the invention in any way. All references cited herein, whether supra or infra, are hereby incorporated by reference in their entirety.

EXAMPLE 1

Ion Channels

Tools for screening ion channels are generated by injection of pooled cDNAs directly into the nucleus of Xenopus oocytes. The expression of the cDNAs is under the control of a cytomeglovirus promoter. Oocytes are known to produce functional ion channels on the cell surface within 24 hours of cDNA injection. Voltage-clamp electrophysiology is used to look for the ion channel of interest, which will be activated by the appropriate selective ligand or by changing the membrane potential of the oocytes. Once an ion channel of interest is detected in injected oocytes, it is characterized using physiological and pharmacological properties that are specific for individual ion channels. In this case it is preferable to functionally identify a single clone that encodes the ion channel of interest so that a mammalian cell line can be made. In most cases, it will be desirable to generate a mammalian cell line for high throughput screening and this is done by testing cells for expression of a phenotype indicative of the ion channel being sought. This may be accomplished by transfecting different pools of cDNA or by multi-iterative pool reduction until only those cDNAs necessary to produce a functional channel have been introduced into the cell. Cells are identified and isolated by methods well known to those skilled in the art. If desired, specific cDNA clones identified by the physiological and pharmacological properties conferred upon host cells, are then subcloned into a mammalian expression vector containing an antibiotic resistance marker, and the resulting plasmid is permanently transfected into the appropriate cell line. This method may be used, for example, with glutamate receptors.

EXAMPLE 2

G-protein Coupled Receptors

The specific approach for G-protein coupled receptors ("GPCRs") depends on the second messenger system with which they are coupled. Screens for GPCRs that activate phospholipase C are generated in a fashion similar to that described for ion channels in oocytes. In oocytes the activation of phospholipase C causes release of calcium from intracellular stores which activates Ca-dependent chloride channels expressed naturally in oocytes. These channels are easy to detect. For other GPCRs, mammalian cell lines are preferable.

In one embodiment cell lines with built-in fluorescent reporter systems are used for host cells. Such cell lines are well known and readily available to those skilled in the art. For example, cell lines that express β-lactamase under control of various second messenger-sensitive promoters can be used for this purpose. These cells change their fluorescent properties upon activation of GPCR second messenger pathways. This change in fluorescence is detectable with a plate reader, or fluorescent microscope, and signals the presence of an active GPCR on the cell surface. One advantage of using fluorescent reporter systems is that a fluorescent-activated cell sorter (FACS) is useful to find the cells that express the GPCR of interest. This is especially advantageous if the transfection of cultured cells is of low efficiency with only a small proportion of the cells showing the pharmacological or physiological activity of interest. The exquisite sensitivity of some reporter systems will markedly speed up the process of expression cloning making it feasible within a time frame suitable for drug discovery. These positive cells are isolated from the rest and developed into a stable cell line. In this way it is possible to generate a permanent cell line ready for screening without further subdivision and testing of the cDNA library. Here again, physiological and pharmacological characterization of the cells provide proof that a screen for the desired protein activity has been attained. This method can be used to set up a screen for any desired protein, for example, the adrenergic alpha-2c receptor or the glucagon-like peptide 1 receptor (GLP-1R), or another example would be the generation of cell lines expressing GABA-B receptor variants.

In another embodiment, cell lines producing a GPCR or any cell surface protein of interest could be identified from a cell pool using antibodies that recognize an extracellular domain of the protein. If the antibody was fluorescently-labeled, a FACS instrument could be used to both identify and isolate cells that produce this protein. An alternative embodiment of the method of the present invention involves the generation and isolation of cells that produce, for example, the GLP-1 receptor, which is a molecular target for diabetes. The endpoint is a cellular fluorescence change based on the binding of a fluorescently labeled ligand specific for this receptor. When bound to such cells, this ligand will render the cells detectable and isolable by a FACS instrument.

EXAMPLE 3

Nuclear Hormone Receptors

One approach useful to identify cells producing specific nuclear hormone receptors ("NHRs") depends on the DNA promoter/promoter element(s) recognized by these ligand-dependent transcription factors. In a variant of the GPCR approach above, cell lines with built-in fluorescent reporter systems that express β-lactamase under control of various promoters modified to contain DNA-binding elements for the NHR of interest are used. In the presence of suitable β-lactamase substrates, these cells change their fluorescent properties following modulation of the NHR protein by interaction with a specific ligand. Again, a FACS instrument is used to identify and also isolate cells that express a NHR of interest. Positive cells isolated from the cell pool are developed into a stable permanent cell line for compound screening. A variation on this approach involves use of a retrovirus carrying a built-in promoter-reporter gene, such that the same viral integration would both activate a chromosomal NHR gene (i.e., for PPAR) and supply a reporter to signal when the desired specific integration event had occurred.

EXAMPLE 4

Ion Channels

Mammalian cells useful for screening ion channels are typically generated by transfection of expression vectors bearing a cloned gene of interest, so that cells produce functional ion channels on the cell surface. Voltage-clamp electrophysiology is often used to detect a particular ion channel, which may be activated by an appropriate selective ligand or by changing the membrane potential of the cell by various means. In the present invention, a cell producing a particular ion channel of interest is identified in a cell pool using various dyes whose intracellular fluorescence is dependent upon the uptake of certain ions from the extracellular medium (or liberation from intracellular stores). Following the proper activation stimulus for the ion channel, altered ion levels in those cells producing the ion channel will cause changes in cell fluorescence which render the cells detectable and isolable by a FACS instrument. Identification of a single cell clone that encodes a particular ion channel gives a more uniform response than would a pool of transfected cells in compound screening. In addition to the FACS approach above, this can be accomplished by similar, less sophisticated means such as multi-iterative pool reduction ("sib selection"). Once identified and isolated by methods well known to those skilled in the art, such specific cell lines are further characterized as to physiological and pharmacological properties conferred upon the host cells.

These are but limited examples of the wide variety of technologies that can be applied to this problem. Improvements in the present methods obvious to those skilled in the art are also covered within the scope of the present invention, for example improvements in expression and recovery of DNA (which may be accomplished with the use of episomal mammalian expression vectors or other viral-based expression systems). Additionally, more sensitive detection methods may also be employed. For example, calcium-sensitive fluorescent dyes can be used to find proteins whose activation leads to increases in intracellular calcium. Reporter systems for each type of signal transduction pathway provide benefits for developing screens against any type of GPCR. Radioligand binding could be used as an endpoint if necessary.

A preferred embodiment of the method of the present invention, for example, involves the cloning of gamma-secretase, which is a molecular target for Alzheimer's Disease. The endpoint is a fluorescence change based on the activity of the secretase enzyme. An artificial fluorescent substrate was introduced into cells. When cleaved by secretase, it migrates to the cell nucleus where it can be specifically detected. This technology is based on fluorescence resonance energy transfer and is uniquely sensitive.

Although the present invention has been described in some detail by way of illustration and example for purposes of clarity and understanding, it will be apparent that certain changes and modifications may be practiced within the scope of the appended claims.

We claim:

1. A method of screening test chemical compounds to identify drug candidates which modulate a functional activity of a specific molecular target, said method comprising the steps of:

(a) introducing a plurality of cDNAs into an appropriate host cell or cells;

(b) testing said host cell or cells to determine if one or more of said cells exhibits a measurable endpoint conferred by the functional activity of the specific molecular target, wherein if one or more of said cells is found to exhibit said measurable endpoint of the specific molecular target, then:
  (i) contacting a cell that exhibits said measurable endpoint with a plurality of test compounds; and
  (ii) detecting whether or not any of said plurality of test compounds modulates said functional activity of the specific molecular target by detecting modulation of a measurable endpoint;

wherein said method does not comprise, before step (b)(ii), a step in which the cDNA of a cell of step (b)(i) is sequenced, and wherein said specific molecular target is an ion channel and a measurable endpoint is change in membrane current flux.

2. The method of claim 1, wherein said method does not comprise, before step (b)(ii), a step in which the expression product of a cDNA of a cell of step (b)(i) is determined.

3. The method of claim 1, wherein the measurable endpoint detected in step (b)(ii) after contact with test compounds is the same measurable endpoint detected in step (b) before contact with test compounds.

4. The method of claim 1 wherein the plurality of cDNAs is obtained by a method of:
  (a) isolating messenger RNA ("mRNA") from tissue known or suspected to express said specific molecular target;
  (b) reverse transcribing said mRNA to produce a library of cDNAs; and
  (c) subcloning said library of cDNAs into an appropriate vector.

5. The method of claim 1 wherein the detecting step comprises detecting whether or not any of said plurality of test compounds decrease or inhibit the activity of the specific molecular target.

6. The method of claim 1 wherein the detecting step comprises detecting whether or not any of said plurality of test compounds activate or enhance the activity of the specific molecular target.

7. The method of claim 1 wherein the cDNA of the cell of step (b)(i) encodes said specific molecular target.

8. A method of screening test chemical compounds to identify drug candidates which modulate a functional activity of a specific molecular target, said method comprising the steps of:

(a) introducing a plurality of cDNAs into an appropriate host cell or cells;

(b) testing said host cell or cells to determine if one or more of said cells exhibits a measurable endpoint conferred by the functional activity of the specific molecular target, wherein if one or more of said cells is found to exhibit said measurable endpoint of the specific molecular target, then:
  (i) contacting a cell that exhibits said measurable endpoint with a plurality of test compounds; and
  (ii) detecting whether or not any of said plurality of test compounds modulates said functional activity of the specific molecular target by detecting modulation of a measurable endpoint;

wherein said method does not comprise, before step (b)(ii), a step in which the cDNA of a cell of step (b)(i) is sequenced, and wherein said host cells or cell is a Xenopus oocyte.

9. The method of claim 8, wherein said method does not comprise, before step (b)(ii), a step in which the expression product of a cDNA of a cell of step (b)(i) is determined.

10. The method of claim 8, wherein the measurable endpoint detected in step (b)(ii) after contact with test compounds is the same measurable endpoint detected in step (b) before contact with test compounds.

11. The method of claim 8 wherein the plurality of cDNAs is obtained by a method of:
  (a) isolating messenger RNA ("mRNA") from tissue known or suspected to express said specific molecular target;
  (b) reverse transcribing said mRNA to produce a library of cDNAs; and
  (c) subcloning said library of cDNAs into an appropriate vector.

12. The method of claim 8 wherein the detecting step comprises detecting whether or not any of said plurality of test compounds decrease or inhibit the activity of the specific molecular target.

13. The method of claim 8 wherein the detecting step comprises detecting whether or not any of said plurality of test compounds activate or enhance the activity of the specific molecular target.

14. The method of claim 8 wherein the cDNA of the cell of step (b)(i) encodes said specific molecular target.

* * * * *